(12) United States Patent
Christoudias

(10) Patent No.: US 8,663,256 B2
(45) Date of Patent: Mar. 4, 2014

(54) METHOD OF HERNIA REPAIR USING SURGICAL MESH

(76) Inventor: George C. Christoudias, Teaneck, NJ (US)

( * ) Notice: Subject to any disclaimer, the term of this patent is extended or adjusted under 35 U.S.C. 154(b) by 0 days.

(21) Appl. No.: 13/592,648

(22) Filed: Aug. 23, 2012

(65) Prior Publication Data

US 2012/0316583 A1 Dec. 13, 2012

Related U.S. Application Data

(62) Division of application No. 11/736,383, filed on Apr. 17, 2007, now Pat. No. 8,343,231.

(51) Int. Cl.
*A61B 17/08* (2006.01)
(52) U.S. Cl.
USPC .......................................................... 606/151
(58) Field of Classification Search
None
See application file for complete search history.

(56) References Cited

U.S. PATENT DOCUMENTS

| 5,456,720 | A | 10/1995 | Schultz et al. |
| 6,596,002 | B2 | 7/2003 | Therin et al. |
| 7,101,381 | B2 | 9/2006 | Ford et al. |
| 2004/0087980 | A1 | 5/2004 | Ford et al. |
| 2005/0043818 | A1 | 2/2005 | Bellon Caneiro et al. |

OTHER PUBLICATIONS

Affidavit of George C. Christoudias, with Exhibits A-F, dated Nov. 29, 2009, in U.S. Appl. No. 11/736,383.
Affidavit of George C. Christoudias, with Exhibits A-H; dated Jan. 29 2010, in U.S. Appl. No. 11/736,388.
Declaration of George C. Christoudias, with Exhibit A, dated Jun. 28, 2012, in U.S. Appl. No. 11/736,383.

*Primary Examiner* — Corrine M McDermott
*Assistant Examiner* — Son Dang
(74) *Attorney, Agent, or Firm* — David M. Quinlan, P.C.

(57) ABSTRACT

A method of laparoscopically repairing a hernia defect comprises inserting into the patient's abdomen a surgical mesh sheet larger than the hernia defect and having a fixation fin with its proximal edge attached to a surface of the sheet. The mesh sheet is manipulated into position with the sheet surface in place at the peritoneal surface of the patient's abdominal wall and the fixation fin disposed in the hernia defect. The method reapproximates opposing edges of the defect by suturing them together with the fixation fin between them, after which the distal edge of the fixation fin is below the external surface of the patient's abdomen. The sheet is then laparoscopically positioned and anchored to the abdominal wall peritoneal surface.

16 Claims, 7 Drawing Sheets

METHOD OF HERNIA REPAIR USING SURGICAL MESH

This application is a division of U.S. application Ser. No. 11/736,383, filed Apr. 17, 2007, which is now U.S. Pat. No. 8,343,231, which is incorporated herein by reference.

The present invention comprises an improved surgical mesh for hernia repair having a fixation fin made of absorbable or non-absorbable surgical material or a combination of both.

In the current art of surgical repair of an incisional or ventral hernia (photograph 1a), a mesh is implanted to reinforce the repair and prevent reoccurrence of the hernia. In the laparoscopic method of hernia repair used by the inventor, the entrance to the peritoneal cavity is gained through an incision through the abdominal wall defect. A port is then inserted through the defect into the abdominal cavity and connected to a $CO_2$ source. A pneumoperitoneum is then established. A laparoscope is then entered into the abdomen through the port. Under video control, three more ports are introduced at three different points away from the hernia defect. The pneumoperitoneum is then evacuated and the port going through the defect is removed.

A surgical mesh of an appropriate size for the size of the defect (photograph 1b) is then inserted through the incision that was made first, over the defect, into the abdominal cavity (photograph 1c). The mesh is then sutured onto the edges of the hernia defect, if the defect is too large to be closed by approximation of the edges of the defect. If the edges of the defect can be approximated primarily by suture, then the mesh is incorporated in the repair. There is excess mesh of at least 4 cm, extending beyond the fixation line (photograph 1d). This excess mesh is then fixed onto the peritoneal surface of the abdominal wall (photographs 2b, 2c and 2d), after closure of the edges of the hernia defect and reestablishment of the pneumoperitoneum. The excess mesh is seen suspended from the suture line (photograph 1d). The mesh is then spread smoothly onto the abdominal wall with a manipulating instrument and fixed in place with a stapling fixation device (photographs 2a, 2b, 2c and 2d).

Some potential problems can arise with this method. The following problems are related to the suturing of the mesh to the abdominal wall defect Injury to the Underlying Intestine and/or Organ.

The intestines and/or organs are resting on the posterior surface of the mesh. The suture fixing the mesh on the defect has to enter through the anterior to posterior surface of the mesh and then through the posterior to the anterior surface of the mesh. The potential for the suture to go through the intestine/organ resting on the posterior surface of the mesh while suturing the mesh is real and can lead to severe consequences resulting from the injury to the intestine/organ.

Placing the Suture Through the Mesh.

If the excess portion of the mesh is lying by the suture site, it could be inadvertently caught by the suture and folded over on itself. This would impede the unfolding and fixation of the mesh onto the abdominal wall, making it necessary to remove the suture of the repair and start the repair all over again, causing unnecessary delays.

Wrinkling of the Mesh by the Suture.

If the suture is not placed in a perfectly straight line on the mesh engaged on the suture line, then wrinkling of the mesh will result. This renders the spreading and fixation of the mesh onto the abdominal wall problematic, compromising perfection.

The present invention comprises an improvement of the currently used surgical hernia repair mesh. The improved mesh will facilitate the fixation of the mesh on the edge of the hernia defect by including a fixation fin, which is incorporated in the repair. This prevents injury to the underlying intestine or other abdominal organs. It further facilitates the spreading of mesh onto the abdominal wall surface in preparation for the fixation of said mesh in place with the appropriate fixation device with staples by providing a central stiff ridge, which extends alongside the midline of the mesh. The stiff ridge maintains the mesh expanded adjacent the ridge and facilitates spreading said mesh and fixing it onto the abdominal wall with the appropriate staples.

A second embodiment comprises an improved surgical mesh, which includes a tubular pocket along the long midline of the mesh with an opening in the center for removal of a flexible mesh spreader from the pocket. A suture or thread is attached to the flexible mesh at the opening of the pocket to facilitate removal of the flexible mesh spreader from the opening.

Accordingly, the object of this invention is to provide a new and improved surgical mesh for hernia repair.

Another object of this invention is to provide a new and improved surgical mesh for hernia repair including a fixation fin extending at a right angle therefrom to facilitate the fixation of the mesh on the edge of the hernia defect to prevent injury to the underlying intestine and other abdominal organs.

A further object of this invention is to provide a new and improved surgical mesh particularly for laparoscopic surgery which includes a fixation fin to facilitate the spreading of mesh onto the abdominal wall surface by providing a central stiff ridge which maintains the mesh expanded adjacent the ridge and facilitates spreading and fixing the body of the mesh onto the abdominal wall with staples while the fin is incorporated in the suturing repair of the defect.

The above and other objects and advantages of the present invention may be more clearly seen when viewed in conjunction with the accompanying drawings wherein.

FIGS. 9A, 9B, 9C, and 9D comprise photographs 1*a*, 1*b*, 1*c*, and 1*d*, respectively, of the actual hernia; and FIGS. 10A, 10B, 10C, and 10D comprise photographs 2*a*, 2*b*, 2*c*, and 2*d*, respectively, of the hernia repair.

Figure 1:
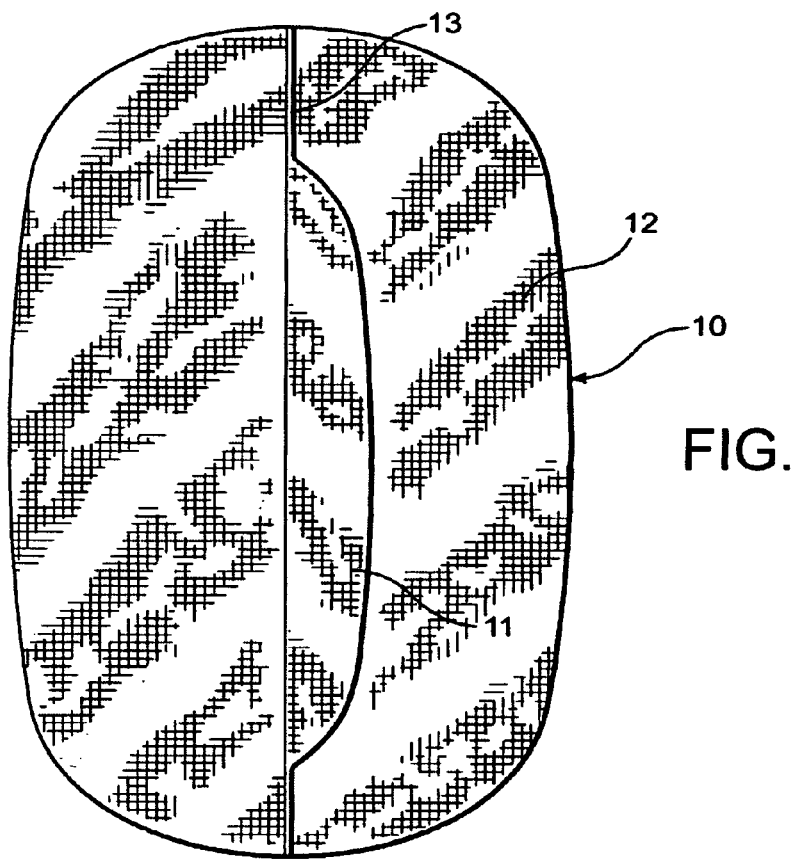
FIG. 1 is a front view of a surgical mesh with a fixation fin and stiff central ridge.
Figure 1A:
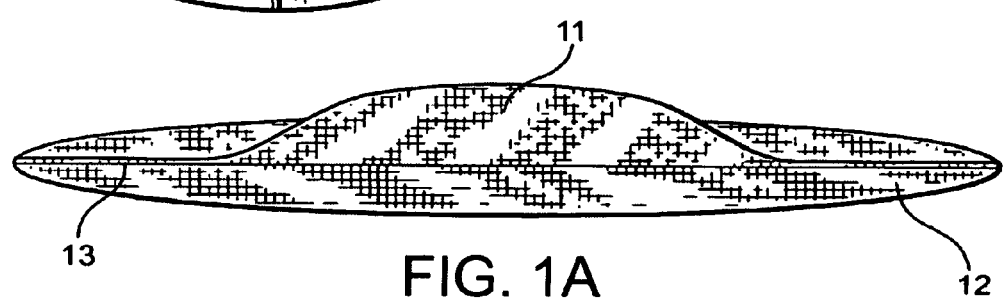
FIG. 1A is a side perspective view of the mesh design shown in FIG. 1.
Figure 1B:
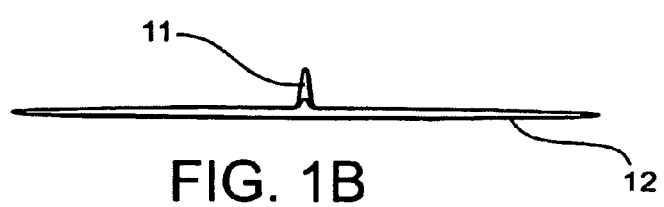
FIG. 1B is an end view of the mesh design shown in FIG. 1.

As shown in the drawings particularly FIGS. 1, 1A, and 1B, the invention comprises a surgical mesh 10 for hernia repair having a fixation fin 11 of absorbable or non-absorbable surgical material mounted thereon. The fin 11 extends at a right angle from one of the surfaces of the main hernia repair mesh 12 usually along the midline 13 of the surface. When the mesh 12 is placed into the abdomen 20, as described in the background of the invention, the fixation fin 11 is projecting in the direction leading away from the abdominal cavity. The mesh 12 can then be fixed onto the defect 14 by suturing the fixation fin 11 and avoiding suturing through the main body of the mesh 12. In this way no needle or suture penetrates the main body of the mesh 12 and this eliminates the danger of a) injury to the bowel layer resting on the posterior surface of the mesh 12; b) catching with the needle and suturing an additional fold of the excess mesh which would impede opening, spreading and fixing the mesh 12; and c) wrinkling the mesh 12 and impeding opening, spreading and fixing the mesh 12.

The present invention further comprises a flexible stiff ridge alongside the midline 13 of the mesh 12, which will lift the mesh 12 alongside the abdominal wall 21 and facilitate the spreading on either side of the mesh 12 and its fixation onto the abdominal wall 21. Said flexible stiff ridge may be made either of absorbable or non-absorbable surgical material and is incorporated alongside the midline of the main body of the mesh 12.

Figures 2, 2C:
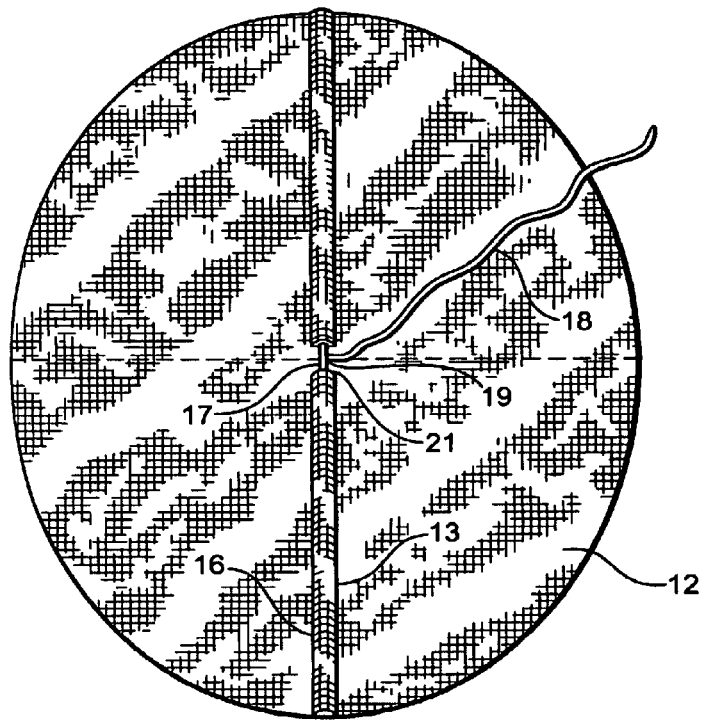
FIG. 2 is a front view of an alternate embodiment of the invention including a tubular midline pocket.
FIG. 2C is a view of the flexible rod and attached thread.
Figure 2A:
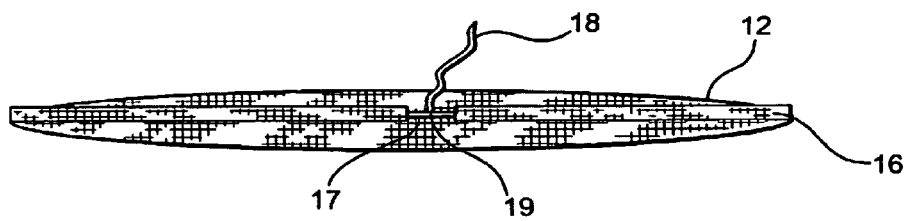
FIG. 2A is a side perspective view of the mesh design shown in FIG. 2.
Figure 2B:
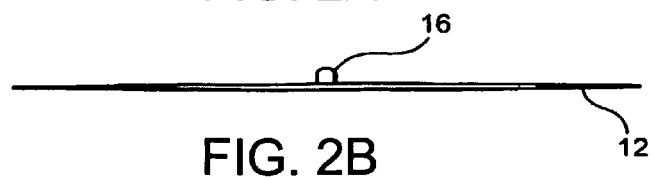
FIG. 2B is an end view of the mesh design shown in FIG. 2.

An alternate embodiment of this invention shown in FIGS. 2, 2A and 2B comprises a tubular elongated structure or pocket 16 extending alongside the midline 13 of the main body of the mesh 12 on one of its surfaces at the center of the mesh 12 allowing the insertion of a thin, removable, flexible rod 17, which, when inserted into the tubular structure 16 of the mesh 12, will maintain said mesh 12 adjacent the rod in an expanded condition. Said rod 17 has a strong thread 18 affixed onto its center 19 and pull on this thread 18 will remove the rod 17 from the mesh tube 16.

Referring now to FIG. 1 of the drawings, the invention comprises an overview of a hernia repair mesh 10 with a main body of the mesh 12, a fixation fin 11 and a central stiff ridge 13. A side view along the axis of the mesh 12 and the short axis of the mesh 12 are also demonstrated.

The alternate embodiment shown in FIG. 2 comprises a mesh 12 with a central tubular structure 16 with an opening 21 at the center. A flexible rod 17 with a thread 18 for removal of said rod 17, is inserted into said tubular structure 16 to maintain the mesh 12 in the expanded positions and facilitate its fixation onto the abdominal wall 21. Once the mesh 12 is fixed, thread 18 is pulled to remove flexible rod 17 from the mesh 12. Flexible rod 17 with disengagement thread 18 is also depicted in FIG. 2C.

FIG. 2A demonstrates a side view of the mesh 12 along the longitudinal axis and FIG. 2B demonstrates the side view of the mesh 12 alongside the short axis of the mesh 12.

Figure 3:
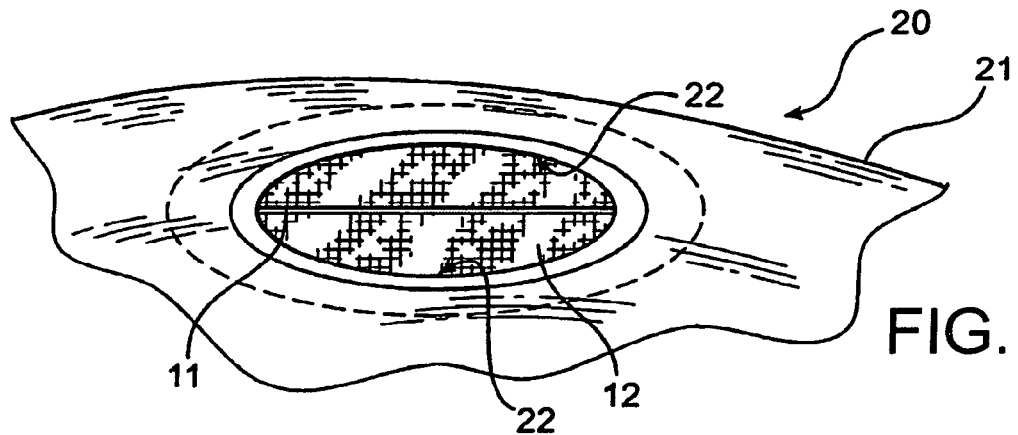
FIG. 3 is a schematic view of the improved mesh inside the abdomen spread on the abdominal wall surface.

FIG. 3 demonstrates the mesh 12 in place inside the abdomen 20 through the hernia defect edges 22 at the depth of the abdominal wall layers 21 and the fixation fin 11 projecting outwardly from the main mesh 12 before approximation of the hernia defect edges 22.

Figure 4:
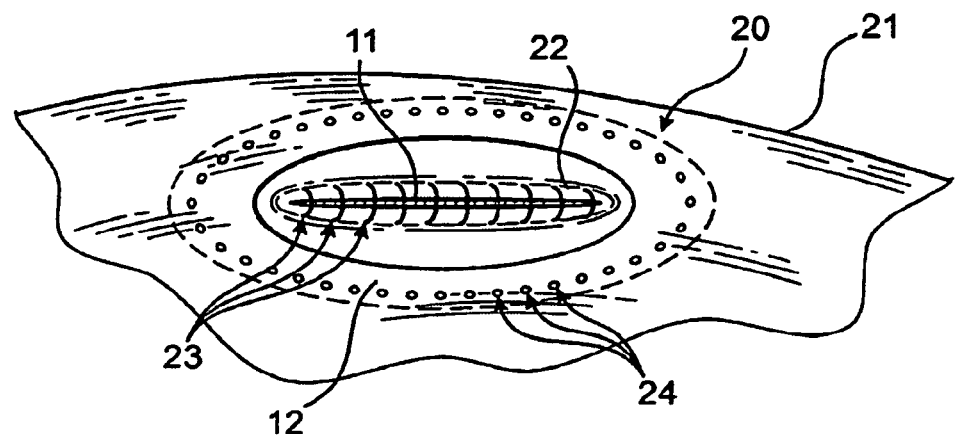
FIG. 4 is a schematic view of the mesh fixed or anchored on the posterior surface of the abdominal wall, as seen from the outside, with the fixation fin incorporated and contained within the suture line of the approximated edges of the hernia defect (see FIG. 8)

FIG. 4 demonstrates the closure of the hernia defect edges 22 with incorporation of the mesh 12 fixation fin 11 with a surgical suture 23 and the mesh 12 fixed inside the abdomen 20 with the appropriate staples 24. The fixation staples 24 are applied laparoscopically with a fixation device on the posterior surface of the abdominal wall 21.

Figure 5:
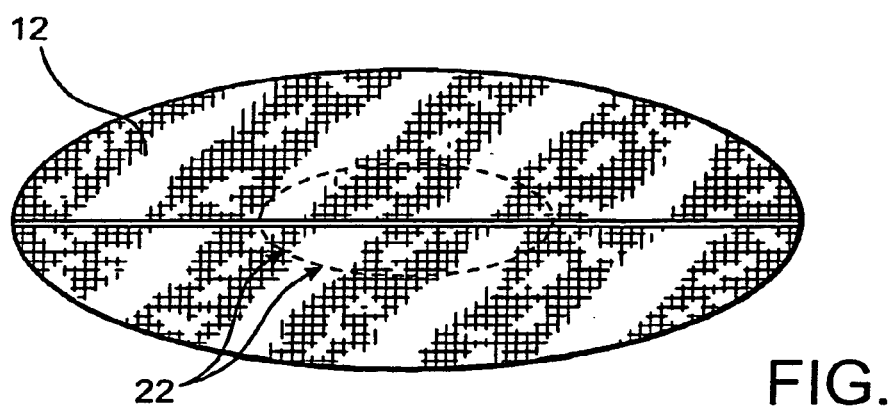
FIG. 5 is a schematic view of the mesh from inside the abdomen viewed laparoscopically.

FIG. 5 demonstrates the mesh 12 viewed from inside the abdomen 20 with the defect location depicted and the central stiff ridge 13 of the mesh 12, which maintains the mesh 12 in the expanded position.

Figure 6:
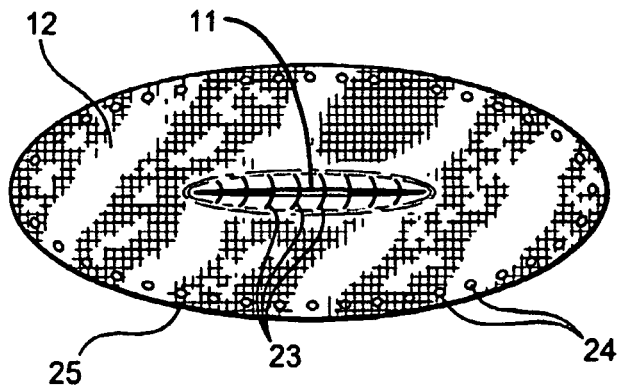
FIG. 6 is a schematic view of the mesh fixed on the posterior surface of the anterior abdominal wall viewed from inside the abdomen.

FIG. 6 demonstrates the mesh 12 viewed from inside the abdomen 20 with the abdominal hernia defect 30 closed and the periphery of the mesh 25 fixed with the appropriate fixation staples 24.

Figure 7:
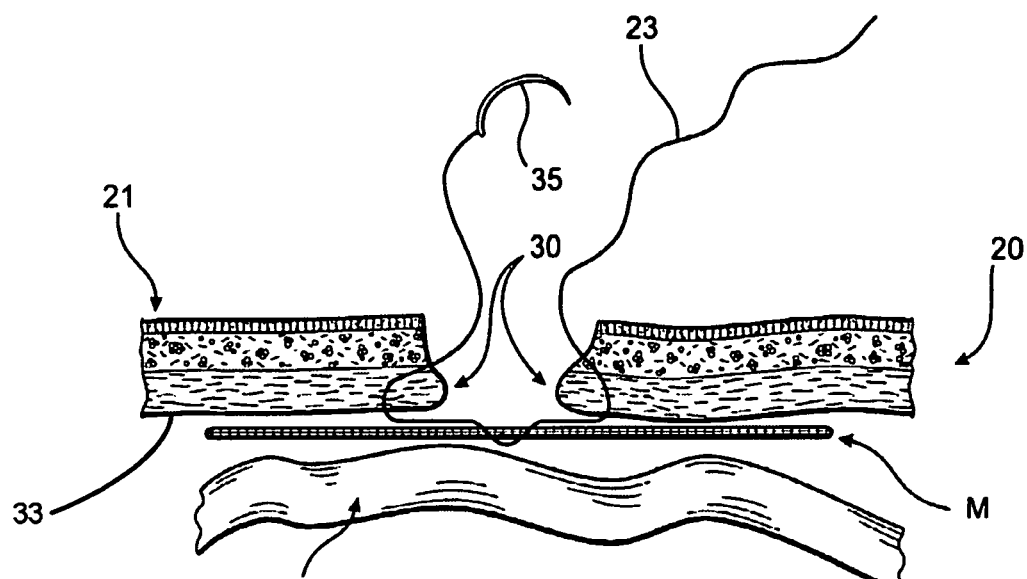
FIG. 7 is a side schematic view of a prior art mesh without a fixation fin in the abdomen to effect a hernia repair.

FIG. 7 is a cross section of the abdomen 20 at the site of an incisional/ventral hernia demonstrating the hernia defect 30 of the abdominal wall 21 with a plurality of layers, with a prior art mesh M without a fixation fin spread over the intestine 37, on the peritoneal surface 33.

By using a needle 35, a suture 23 is passed through the edges of the defect 22, and the center of the prior art mesh M.

Figure 7A:
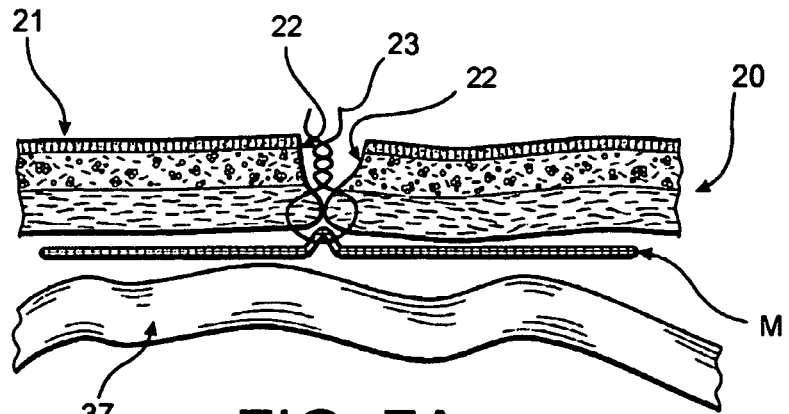
FIG. 7A shows schematically the suture of FIG. 7 tied approximating the hernia defect and incorporating the center of the prior art mesh without a fixation fin to close the edges of the hernia defect.

FIG. 7A demonstrates the same cross-section of the abdomen 20 with the suture 23 tied, the edge of the hernia defect closed and the center of the mesh M fixed onto the closed hernia defect edges 22 by the same suture 23. The center of the mesh M is wrinkled as a result of the pull by the tied suture 23. This is a problem with the prior art.

Figure 8:
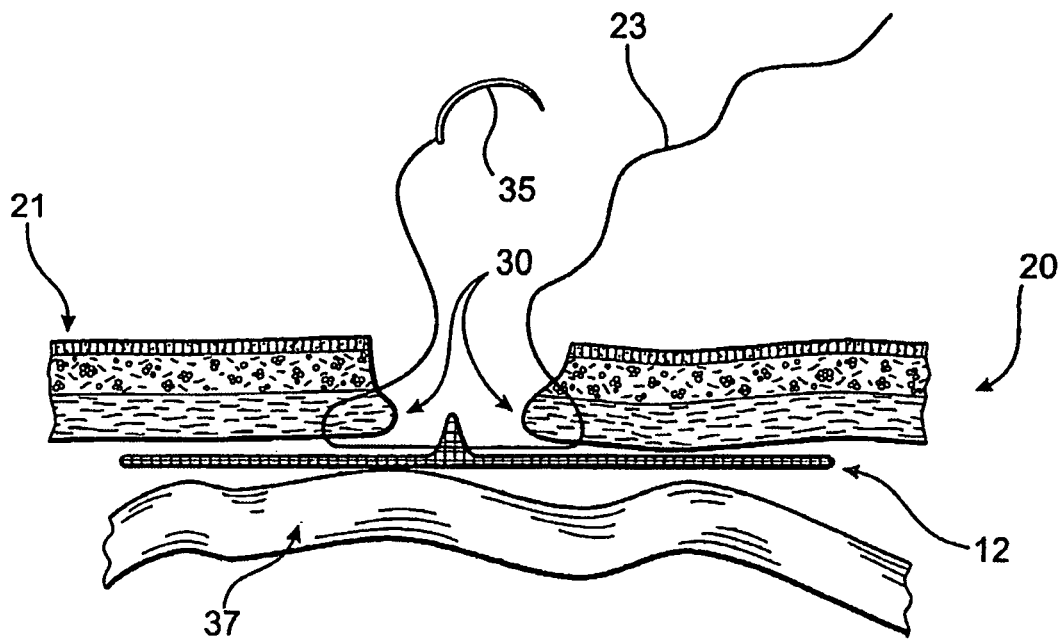
FIG. 8 shows schematically a side view of the hernia repair with suturing through the opposing edges of the defect and the fixation fin.
Figure 8A:
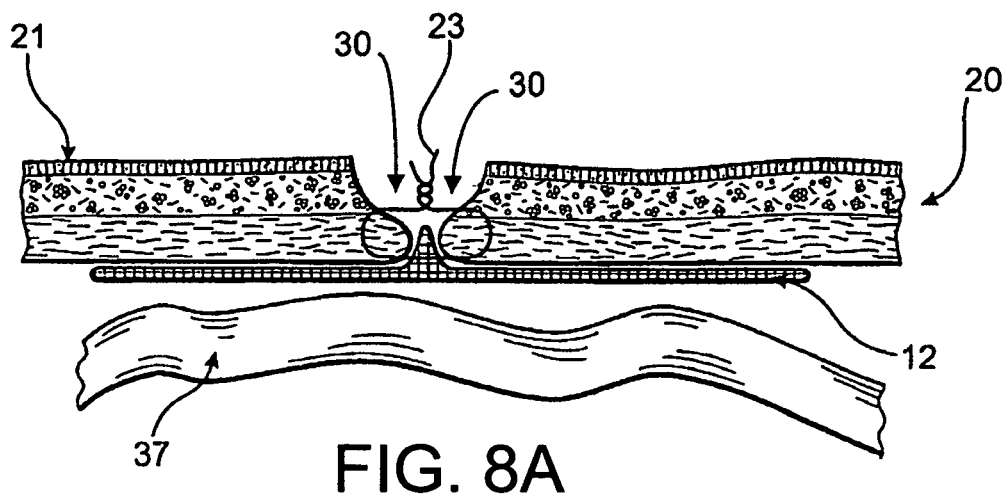
FIG. 8A shows schematically the suture of FIG. 8 tied approximating the hernia defect and incorporating the fixation fin, which is contained within the suture line of the reapproximated edges if the defect.
Figure 9A:
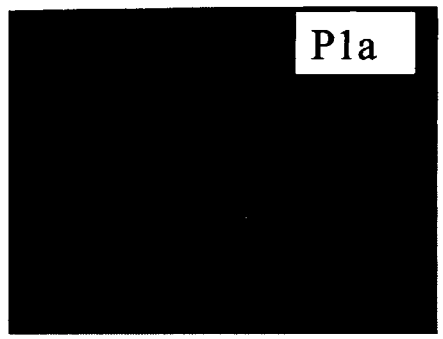
Figure 9B:
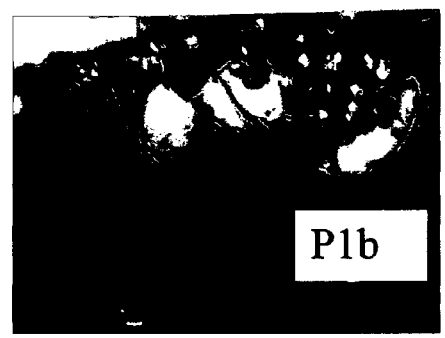
Figure 9C:
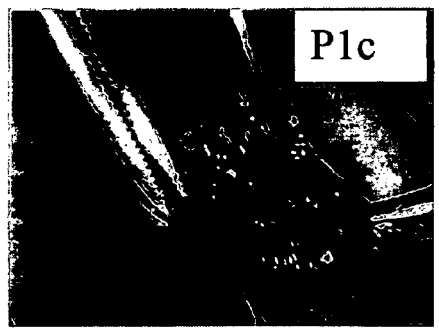
Figure 9D:
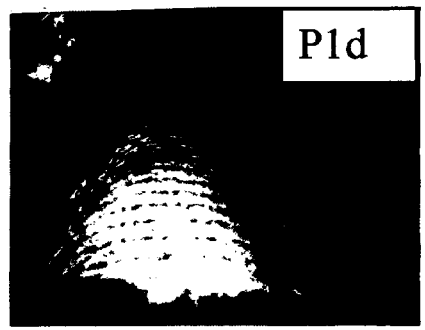
Figure 10A:
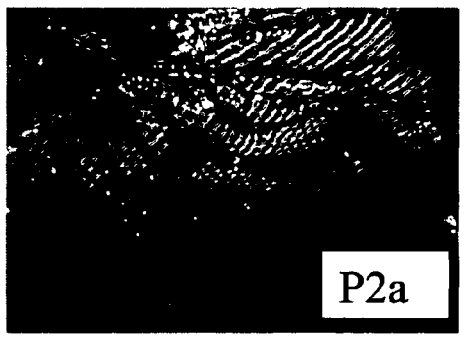
Figure 10B:
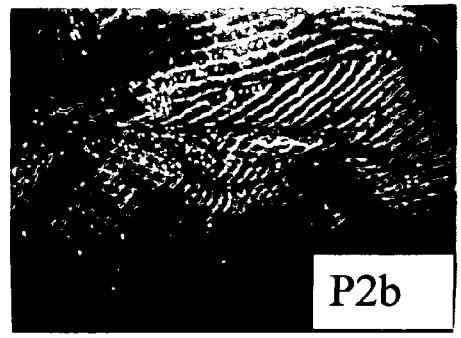
Figure 10C:
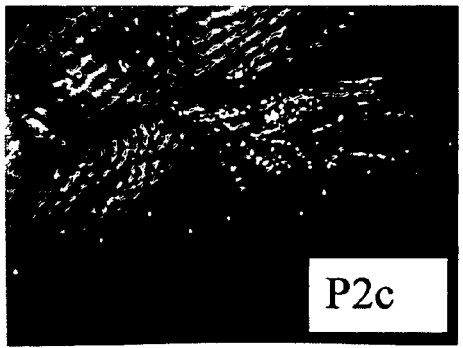
Figure 10D:
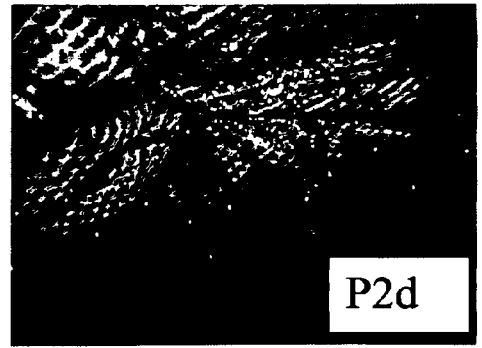

FIG. 8 is a cross-section of the abdomen 20 as in FIG. 7 with the only difference being that the mesh 12 has the fixation fin 11 of the new and improved mesh 12. The suture 23 is passed through the opposing edges of the defect and the fixation fin 11, instead of the center of the main body of the mesh 12. The fixation fin is incorporated and contained within the reapproximated edges of the hernia defect, as seen in FIG. 8A. Potential problems and injury are thus prevented.

While the invention has been explained by a detailed description of certain specific embodiments, it is understood that various modifications and substitutions can be made in any of them within the scope of the appended claims that are intended also to include equivalents of such embodiments.

What is claimed is:

1. A method of laparoscopically repairing a hernia defect in a patient's abdominal wall, the method comprising:

inserting into the patient's abdomen a surgical mesh comprising a sheet of mesh material having an extent greater than the size of the hernia defect and a fixation fin with a proximal edge attached to a surface of the sheet and extending along the sheet for a distance less than the extent thereof and a distal edge raised above the sheet surface a sufficient distance to permit attachment of the fixation fin to opposing edges of a hernia defect when the sheet is in place inside the patient's abdomen;

manipulating the surgical mesh into position with the sheet in place at the peritoneal surface of the patient's abdominal wall and the fixation fin disposed in the hernia defect;

reapproximating opposing edges of the hernia defect by suturing them together with the fixation fin therebetween, wherein the distal edge of the fixation fin is spaced below the external surface of the patient's abdominal wall after suturing the fixation fin between the reapproximated edges of the hernia defect and the sheet extends beyond the proximal edge of the fixation fin in all directions a sufficient distance to allow the sheet to be anchored to the peritoneal surface of the patient's abdominal wall at any desired location on the sheet;

thereafter laparoscopically positioning the sheet surface to lie proximate to the peritoneal surface of the patient's abdominal wall; and anchoring the sheet to the peritoneal surface of the abdominal wall at selected locations around the surgical mesh.

2. A method as in claim 1, wherein the hernia defect comprises a single opening in a patient's abdominal wall.

3. A method as in claim 1, wherein the anchoring step is performed laparoscopically.

4. A method as in claim 1, wherein no location on the peripheral edge of the sheet is closer than about four cm to the proximal edge of the fixation fin.

5. A method as in claim 1, wherein the sheet includes a stiffening ridge extending along a line on the sheet for assisting laparoscopic placement of the sheet, the fixation fin proximal edge is attached to the stiffening ridge with the distal edge of the fixation fin raised above the surface a greater distance than the stiffening ridge, and the stiffening ridge extends along the line on the sheet in at least one direction beyond the proximal edge of the fixation fin.

6. A method as in claim 5, wherein the stiffening ridge and the fixation fin are a single structure.

7. A method as in claim 5, wherein the surgical mesh is a one-piece structure and the sheet is continuous.

8. A method as in claim 5, wherein the stiffening ridge extends in both directions beyond the proximal edge of the fixation fin.

9. A method as in claim 8, wherein the stiffening ridge is straight and extends to the edges of the sheet, and the proximal edge of the fixation fin is attached to the stiffening ridge and is raised above the surface a greater distance than the stiffening ridge.

10. A method as in claim 9, wherein the straight edge bisects the surface of the sheet and the sheet is laparoscopically anchored to the peritoneal surface of the abdominal wall at locations proximate to the stiffening ridge.

11. A method as in claim 5, wherein the sheet, the stiffening ridge, and the fixation fin are a one-piece structure.

12. A method as in claim 11, wherein the sheet is continuous.

13. A method as in claim 1, wherein the sheet is inserted into the patient's abdomen through the hernia defect.

14. A method as in claim 13, wherein the sheet includes a stiffening ridge extending along a line on the sheet for assisting laparoscopic placement of the sheet, the fixation fin proximal edge is attached to the stiffening ridge with the distal edge of the fixation fin raised above the surface a greater distance than the stiffening ridge, and the stiffening ridge extends along the line on the sheet in at least one direction beyond the proximal edge of the fixation fin.

15. A method as in claim 14, wherein the surgical mesh is a one-piece structure and the sheet is continuous.

16. A method as in claim 1, wherein the fixation fin extends substantially the entire length of the reapproximated edges of the hernia defect and the reapproximating step includes suturing the fixation fin and the opposing edges of the hernia defect at a plurality of locations.

* * * * *